(12) United States Patent
Woldegebriel et al.

(10) Patent No.: US 11,571,169 B2
(45) Date of Patent: Feb. 7, 2023

(54) PROBABILITY-BASED DETECTOR AND CONTROLLER APPARATUS, METHOD, COMPUTER PROGRAM

(71) Applicant: Nokia Technologies Oy, Espoo (FI)

(72) Inventors: Michael Woldegebriel, Espoo (FI); Harri Lindholm, Helsinki (FI)

(73) Assignee: Nokia Technologies Oy, Espoo (FI)

( * ) Notice: Subject to any disclaimer, the term of this patent is extended or adjusted under 35 U.S.C. 154(b) by 249 days.

(21) Appl. No.: 16/954,031

(22) PCT Filed: Dec. 18, 2018

(86) PCT No.: PCT/EP2018/085455
§ 371 (c)(1),
(2) Date: Jun. 15, 2020

(87) PCT Pub. No.: WO2019/121655
PCT Pub. Date: Jun. 27, 2019

(65) Prior Publication Data
US 2021/0161479 A1    Jun. 3, 2021

(30) Foreign Application Priority Data
Dec. 22, 2017   (EP) .................................... 17210461

(51) Int. Cl.
*A61B 5/00*       (2006.01)
*G16H 50/20*      (2018.01)
(Continued)

(52) U.S. Cl.
CPC ............ *A61B 5/7275* (2013.01); *A61B 5/349* (2021.01); *A61B 5/746* (2013.01); *G06K 9/6232* (2013.01);
(Continued)

(58) Field of Classification Search
CPC ....... A61B 5/7275; A61B 5/349; A61B 5/746; A61B 5/7282; G06K 9/6232;
(Continued)

(56) References Cited

U.S. PATENT DOCUMENTS

| 6,678,548 B1 | 1/2004 | Echauz et al. ................ 600/544 |
| 2007/0276279 A1* | 11/2007 | Echauz ................. G16H 50/30 600/544 |

(Continued)

OTHER PUBLICATIONS

De Oliveira, Lorena S.C., et al. "Premature Ventricular Beat Classification Using a Dynamic Bayesian Network", IEEE Engineering in Medicine and Biology Society, 2011, abstract, 1 pg.
(Continued)

*Primary Examiner* — Jianxun Yang
(74) *Attorney, Agent, or Firm* — Harrington & Smith (57) ABSTRACT

An apparatus including circuitry configured to determine a probability by combining at least: a probability that an event is present within a current feature of interest given a first set of previous features of interest, and a probability that the event is present within the current feature of interest given a second set of previous features of interest, different to the first set of previous features of interest; circuitry configured to detect the event based on the determined probability; and circuitry configured to control, in dependence on the detection of the event, performance of an action.

18 Claims, 4 Drawing Sheets

(51) Int. Cl.
*A61B 5/349* (2021.01)
*G06K 9/62* (2022.01)
*G06N 7/00* (2006.01)

(52) U.S. Cl.
CPC ......... *G06K 9/6296* (2013.01); *G06K 9/6298* (2013.01); *G06N 7/005* (2013.01); *G16H 50/20* (2018.01)

(58) Field of Classification Search
CPC .... G06K 9/6296; G06K 9/6298; G06N 7/005; G06N 5/045; G16H 50/20
See application file for complete search history.

(56) References Cited

U.S. PATENT DOCUMENTS

2008/0183093 A1* 7/2008 Duann .................. A61B 5/35
  600/521
2009/0270939 A1 10/2009 Shaquer et al. ................ 607/30

OTHER PUBLICATIONS

Woldegebriel, Michael, et al., "Artificial Neural Network for Probabilistic Feature Recognition in Liquid Chromatography Coupled to High-Resolution Mass Spectrometry", Analytical Chemistry, Jan. 17, 2017, abstract, 1 pg.

* cited by examiner

PROBABILITY-BASED DETECTOR AND CONTROLLER APPARATUS, METHOD, COMPUTER PROGRAM

CROSS REFERENCE TO RELATED APPLICATION

This patent application is a U.S. National Stage application of International Patent Application Number PCT/EP2018/085455 filed Dec. 18, 2018, which is hereby incorporated by reference in its entirety, and claims priority to EP 17210461.4 filed Dec. 22, 2017.

TECHNOLOGICAL FIELD

Embodiments of the present invention can relate to a probability-based detector and controller apparatus, method, and/or computer program. In particular, some embodiments relate to detecting an event based on a determined probability and controlling performance of an action in dependence upon the detection of the event. This may find application, for example, in the automated detection of anomalies in measurements and the consequent automated generation of an alert. This may, for example, be used for monitoring systems, failure detection, biological signal monitoring.

BACKGROUND

In simple well-constrained systems, it may be possible to model the system deterministically. That is, by measuring a set of specific parameters of an implicit or explicit model, and using those parameters in the model, an occurrence of an event causally linked to that set of parameters can be determined. In this situation, it is possible to measure a limited, well-defined set of parameters to determine events.

In more complex or less well-constrained systems, there may be no known model. It may not be known what parameters influence an event or the extent to which they influence an event either individually or in combination. Any model may be specific to unknowns that are dependent on context, for example, features of the system, the system's history, the current time etc.

For example, how can it be determined that a biological signal measured for a subject is normal or abnormal?

For example, how can it be determined that a measured signal indicates imminent failure of a system?

It would be desirable to detect an event within measured data based on a determined probability and then control performance of an action in dependence upon the detection of the event.

Such automation may be used to reduce or eliminate the need for review by a trained human expert and/or may enable detection not achievable by a human.

This may be particularly useful in monitoring applications when it is desirable to collect data to identify or predict events.

BRIEF SUMMARY

According to various, but not necessarily all, embodiments of the invention there is provided an apparatus comprising:
means for determining a probability by combining at least:
a probability that an event is present within a current feature of interest given a first set of previous features of interest, and
a probability that the event is present within the current feature of interest given a second set of previous features of interest, different to the first set of previous features of interest;
means for detecting the event based on the determined probability; and
means for controlling, in dependence on the detection of the event, performance of an action.

In some but not necessarily all examples, a current feature of interest is a feature of interest of a current data portion, a previous feature of interest is the same feature of interest as the current feature of interest but is of a previous data portion, and previous features of interest are the same feature of interest as the current feature of interest but are of respective previous data portions.

In some but not necessarily all examples, the first set of previous features of interest is smaller than the second set of previous features of interest.

In some but not necessarily all examples, the first set of previous features of interest consists of an immediately previous feature of interest and the second set of previous features of interest consists of a sequence of immediately previous features of interest.

In some but not necessarily all examples, the probability that an event is present within a current feature of interest given a first set of previous features of interest, is based on a probability of the current feature of interest given the event, based on the first set of previous features of interest, and a probability of the event.

In some but not necessarily all examples, the probability that an event is present within a current feature of interest given a first set of previous features of interest is based on: a likelihood based on evidence from the first set of previous features of interest and a current data portion, and a probability of the event.

In some but not necessarily all examples, the probability that the event is present within the current feature of interest given a second set of previous features of interest, different to the first set of previous features of interest is based on a probability of the current feature of interest given the event, based on the second set of previous features of interest, and a probability of the event.

In some but not necessarily all examples, the probability that the event is present within the current feature of interest given a second set of previous features of interest, different to the first set of previous features of interest is based on: a likelihood based on evidence from the second set of previous features of interest and the current data portion, and a probability of the event.

The likelihood may, for example, based on a belief based on a previous probability density function wherein the previous probability density function is based on the second set of previous features of interest.

The previous probability density function may be based on a combination of probability density functions and/or the previous probability density function is based on a Bayesian update of a probability density function.

In some but not necessarily all examples, the probability that an event is present within a current feature of interest given a first set of previous features of interest is marginalized with respect to multiple scenarios for the event and wherein the probability that the event is present within the current feature of interest given a second set of previous features of interest is marginalized with respect to the same multiple scenarios for the event.

In some but not necessarily all examples, combining the probability that an event is present within a current feature of interest given a first set of previous features of interest and the probability that the event is present within the current feature of interest given a second set of previous features of interest, different to the first set of previous features of interest, is part of combining a probability that an event is present within a current feature of interest given a different set of $N_m$ previous features of interest, for a number of different sets m=1 to M, wherein the combination formed is marginalized with respect to the different sets.

The apparatus may comprise means for varying the number of different sets M. In some but not necessarily all examples, the apparatus may comprise means for varying automatically the number of different sets M.

In some but not necessarily all examples, the apparatus may comprise means for, in a current iteration, combining a current probability density function based on the current feature of interest with a previous probability density function based on a set of previous features of interest to create, for a next iteration, a previous probability density function based on the set of previous features of interest and, means for, in the next iteration, using the created previous probability density function in the creation of at least a probability that an event is present within a current feature of interest given a particular set of previous features of interest.

In some but not necessarily all examples, the detected event is an anomaly and the action is an alert, and wherein the apparatus is configured to detect the anomaly and configured to provide the alert.

In some but not necessarily all examples there is provided a system monitoring apparatus, comprising the apparatus, wherein the detected event is indicative of an anomaly in or failure of the system and wherein the system monitoring apparatus is configured to generate as an output an alert signal indicative of an anomaly in or failure of the system.

In some but not necessarily all examples there is provided a health monitoring apparatus, comprising an electrocardiogram sensor and the apparatus wherein the detected event is indicative of an anomaly in a sensed electrocardiogram.

According to various, but not necessarily all, embodiments of the invention there is provided a method of controlling performance of an action in dependence upon detection of an event comprising:
determining a probability by combining:
  a probability that an event is present within a current feature of interest given a first set of previous features of interest, wherein the current feature of interest is a feature of interest of a current data portion and
  a probability that the event is present within the current feature of interest given a second set of previous features of interest, different to the first set of previous features of interest and wherein the previous features of interest are the feature of interest of previous data portions;
detecting the event based on the determined probability; and
in dependence on the detection of the event, controllably performing an action.

According to various, but not necessarily all, embodiments of the invention there is provided a computer program that when run on a processor enables the processor to control performance of an action in dependence upon detection of an event by performing or causing:
determining a probability by combining:
  a probability that an event is present within a current feature of interest given a first set of previous features of interest, wherein the current feature of interest is a feature of interest of a current data portion and
  a probability that the event is present within the current feature of interest given a second set of previous features of interest, different to the first set of previous features of interest and wherein the previous features of interest are the feature of interest of previous data portions;
detecting the event based on the determined probability; and
in dependence on the detection of the event, controllably performing an action.

According to various, but not necessarily all, embodiments of the invention there is provided an apparatus comprising:
at least one processor; and
at least one memory including computer program code
the at least one memory and the computer program code configured to, with the at least one processor, cause the apparatus 200 at least to perform:
producing a determined probability by combining:
  a probability that an event is present within a current feature of interest given a first set of previous features of interest, wherein the current feature of interest is a feature of interest of a current data portion and
  a probability that the event is present within the current feature of interest given a second set of previous features of interest, different to the first set of previous features of interest and wherein the previous features of interest are the feature of interest of previous data portions;
detecting the event based on the determined probability; and
in dependence on detecting the event, controllably performing an action.

According to various, but not necessarily all, embodiments of the invention there is provided a computer program that when run on a processor enables the processor to control performance of an action in dependence upon detection of an event by performing or causing performance of:
determining a probability by combining:
  a probability that an event is present within a current feature of interest given a first set of previous features of interest, wherein the current feature of interest is a feature of interest of a current data portion and
  a probability that the event is present within the current feature of interest given a second set of previous features of interest, different to the first set of previous features of interest and wherein the previous features of interest are the feature of interest of previous data portions;
detecting the event based on the determined probability; and
in dependence on the detection of the event, controllably performing an action.

According to various, but not necessarily all, embodiments of the invention there is provided examples as claimed in the appended claims.

BRIEF DESCRIPTION

For a better understanding of various examples that are useful for understanding the detailed description, reference will now be made by way of example only to the accompanying drawings in which.

DETAILED DESCRIPTION

A Primer in Bayes Theorem

Bayes theorem describes the probability of an event based on ("given") prior knowledge of evidence that might be related to the event.

$$P(A|B)=[P(B|A)*P(A)]/P(B)$$

where A and B are events and $P(B) \neq 0$.

P(A) is the 'prior' probability of event A. It is the independent probability of event A occurring.

P(B) is the 'prior' probability of event B. It is the independent probability of event B occurring.

P(A|B) is the conditional probability of event A occurring given that event B occurs.

P(B|A) is the conditional probability of event B occurring given that event A occurs.

In a Bayesian interpretation, probability means a degree of belief and Bayes Theorem links the degree of belief in a proposition before and after accounting for evidence.

In a Bayesian Inference interpretation, a Bayesian Framework, P(A|B) is a posterior probability as a consequence of two antecedents—a prior probability and a likelihood function derived from the observed data (evidence):

A is a hypothesis H whose probability may be affected by evidence.

B is new data d ("current data").

Therefore $$P(H|d)=[P(d|H)*P(H)]/P(d)$$

P(H) is the prior probability. This is the estimate of the probability of H before the new data d.

P(H|d) is the posterior probability which is the probability of H "given" d, i.e. the probability of H being true given d is observed.

P(d|H) is the likelihood which is the probability of observing d "given" H is true. It indicates a compatibility of the data with the given hypothesis.

P(d) is a constant for all possible hypotheses.

Thus the posterior probability of a hypothesis is proportional to its prior probability and the likelihood (it's compatibility with the new observed evidence).

In Bayesian updating, the posterior probability becomes the prior probability in a subsequent iteration.

In a Bayesian network, the data d may arise from different sources $s_i$.

$$P(H|d)=P(H|s_1 \& s_2 \ldots s_n)=P(s_1 \& s_2 \ldots s_n|H) \cdot P(H)|P(s_1 \& s_2 \ldots s_n)$$

This can be presented as a network (e.g. a directed acyclic graph).

For example, if it is assumed $s_i$ are independent given H then $$P(s_1 \& s_2 \ldots s_n|H)=P(s_1|H) \cdot P(s_2|H) \cdot \ldots P(s_n|H)$$

This can be represented as a simple graph (network) where a node associated with $P(s_1 \& s_2 \ldots s_n|H)$ is interconnected to separate nodes each representing one of $P(s_1|H)$, $P(s_2|H) \ldots P(s_n|H)$ that are not otherwise interconnected.

The general form $P(H|s_1 \& s_2 \ldots s_n)$ can be represented by a more complex directed acyclic graph (network).

If the posterior probability distribution is in the same family as the prior probability distribution, they are conjugate distributions, and the prior is a "conjugate prior" for the likelihood function. For example, the Gaussian family is conjugate to itself (or self-conjugate). If the likelihood function is Gaussian, using a Gaussian prior will produce a posterior distribution that is also Gaussian.

A probability density function (PDF) is a function of a variable. A sample value of the PDF at any of the possible values of the variable provides a relative likelihood that a value of the variable would equal that sample value. Equivalent expressions of likelihood may be used instead of a PDF.

Figure 1:
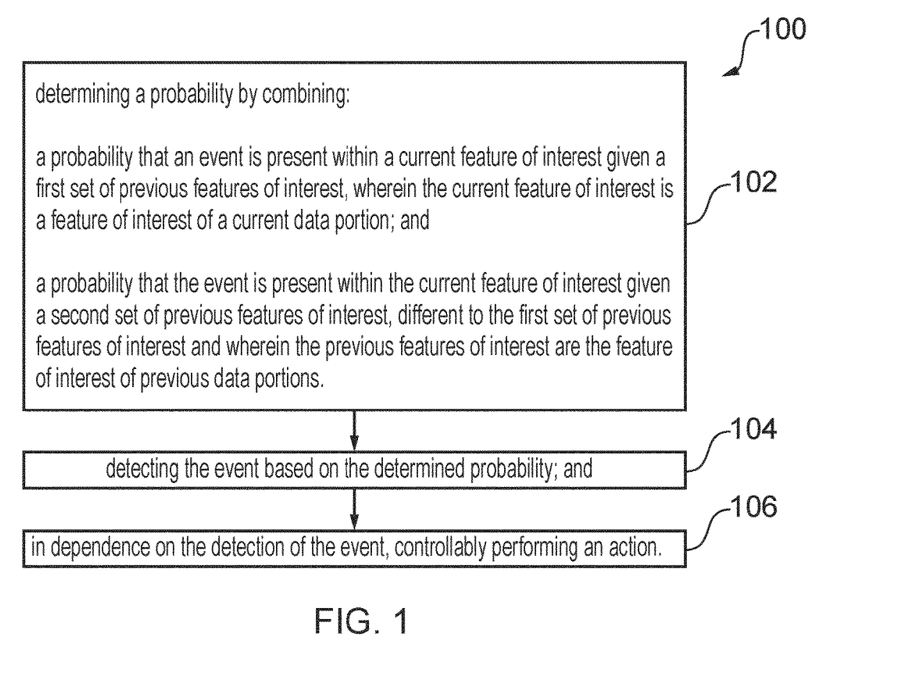
FIG. 1 illustrates an example of a method.

FIG. 1 illustrates an example of a method 100. The example method 100 detects an event and controls performance of an action in dependence upon detection of the event.

The method 100 comprises determining a probability (block 102); detecting the event based on the determined probability (block 104); and, in dependence on the detection of the event, controllably performing an action (block 106).

The block 102, 104, 106 may be automated such that the method comprises:

determining a probability (block 102); then automatically detecting the event based on the determined probability (block 104); and, in dependence on the detection of the event, automatically controllably performing an action (block 106).

In this example, the probability is determined by block 102 by combining:

a probability that an event is present within a current feature of interest given a first set of previous features of interest, and a probability that the event is present within the current feature of interest given a second set of previous features of interest, different to the first set of previous features of interest.

The probabilities are combined at block 102. The probabilities are similar in that they relate to a probability that an event is present within the same current feature of interest given evidence. The probabilities are different in that the evidence is different.

For a first probability, the evidence is a first set of previous features of interest. For a second probability, the evidence is a second set of previous features of interest. The second set of previous features of interest is different to the first set of previous features of interest. In some but not necessarily all examples, the first set is smaller than the second set.

The current feature of interest is a feature of interest of a current data portion. A previous feature of interest is the same feature of interest of a previous data portion. Previous features of interest are the same feature of interest of respective previous data portions.

Figure 2:
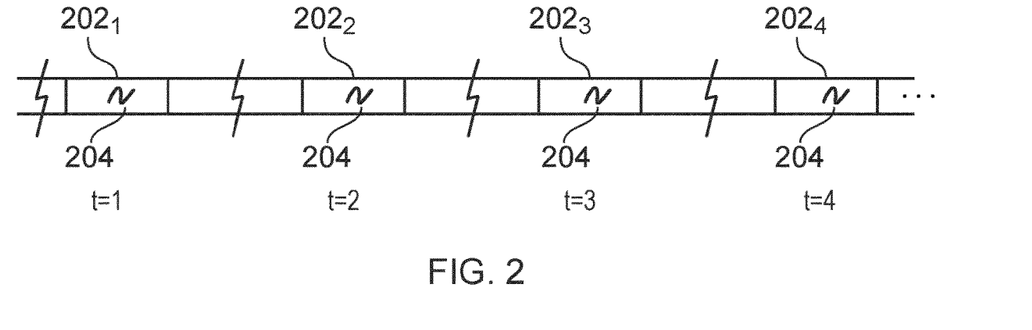
FIG. 2 illustrates an example of a time-separated sequence of data portions.

FIG. 2 illustrates an example of a time-separated sequence of data portions 202. A data portion is measured at a period of time $t_m$ exclusive to that data portion $202_m$. That is the data portions 202 do not overlap in time.

In FIG. 2, the data portion $202_1$ is measured at time $t_1$, then the data portion $202_2$ is measured at time $t_2$, then the data portion $202_3$ is measured at time $t_3$, then the data portion $202_4$ is measured at time $t_4$, etc The data portions 202 have in common the same feature of interest 204, although it may have a different form in each data portion 202. The feature of interest 204 may occur one or more times within each data portion 202.

In some examples, a data portion $202_i$ at time $t_i$ may, for example be determined, by detecting a likely feature of interest at that time within measured data. In other examples, a data portion $202_i$ may be selected on other criteria such as time elapsed.

In some examples, the feature of interest 204 is a recurrent feature of interest 204 that recurs, perhaps periodically within a data portion $202_i$. In this example, the current feature of interest 204 for the current data portion $202_n$ may be a probabilistic construct, for example as a probability density function (PDF), based on similarities and differences between the multiple samples of the recurrent feature of interest 204 within the current data portion $202_n$.

If the current time, in FIG. 2 is time $t_n$, then the current feature of interest is a feature of interest 204 of the current data portion $202_n$. A previous feature of interest is the same feature of interest 204 of a previous data portion $202_{n-1}$, $202_{n-2}$, $202_{n-3}$. Previous features of interest are the same feature of interest 204 of a group of respective previous data portions $202_{n-1}$, $202_{n-2}$, $202_{n-3}$ . . . .

The first and second probabilities are similar in that they relate to a probability that an event is present within the same current feature of interest 204 given evidence. The probabilities are different in that the evidence is different. For the first probability, the evidence is a first set of previous data portions and for the second probability the evidence is a second set of previous data portions.

In the particular example discussed below, but not necessarily all examples, the first set of previous features of interest $S_1$ consists of the immediately previous feature of interest and the second set of previous features of interest consists of a sequence of immediately previous features of interest. The immediately previous feature of interest is the same feature of interest 204 in the immediately previous data portion $202_{n-1}$. A sequence of immediately previous features of interest is the same feature of interest 204 in the immediately previous sequence of data portions $202_{n-1}$, $202_{n-2}$, $202_{n-3}$.

The first and second probabilities in this example are different in that the evidence is 'local' for the first probability because it is immediately preceding and is 'global' for the second probability because it extends over a longer timeframe. Local evidence may emphasise short-term similarities and variations. Global evidence may emphasise longer-term similarities and variations.

Figure 3:
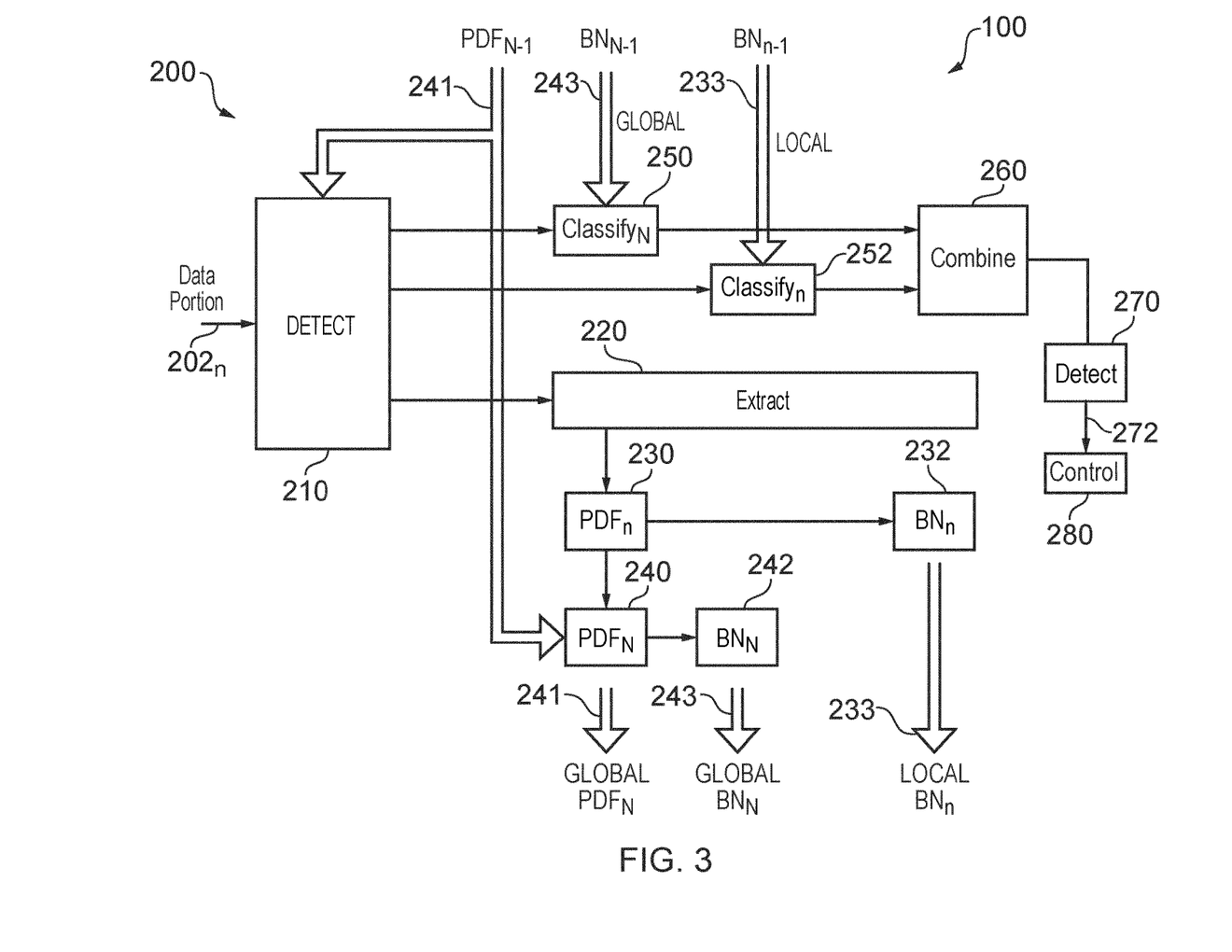
FIG. 3 illustrates an example of the method performed by a system and the system performing the method.

FIG. 3 illustrates an example of the method 100 performed by a system 200 and a system 200 suitable for performance of the method 100. The system 200 is illustrated as a number of blocks. The system 200 controls at block 280 performance of an action in dependence upon detection of an event at block 270 based on a combined probability determined at block 260.

The figure illustrates the system operating at time $t_n$. The current data portion is data portion $202_n$.

The operation of the system 200 illustrated in FIG. 3 will now be escribed for the purpose of anomaly (A) detection.

The system is designed to probabilistic combine evidence that relates to different timescales. There may be differently defined timescales and the definition of the timescales and their number may vary over time. The system creates a belief network BN for each timescale that is propagated for use in the next iteration. The system uses the belief networks BN for each timescale that have been propagated from the previous iteration to determine the probability of an anomaly given the current data portion $202_n$.

There is a classification block 250, 252 . . . for each timescale that classifies a data portion $202_n$ producing at least a probability of the data given the belief network $BN_{N-1}$ (for an anomaly).

The combiner block 260 determines the probability of an anomaly given the current data portion $202_n$ using a probability of the data given there is an anomaly (P(D|A)). For this expression, a parameter representing a belief network (BN) of anomaly can be introduced and marginalized by contemplating different case scenarios such as $BN_{N-1}$ (for an anomaly) and $BN_{n-1}$ (for an anomaly).

The system 200, at block 210, performs automatic detection of relevant region of interest from data portion $202_n$. This may be achieved using a number of different methods such as regression, deep learning, machine learning etc.

The system 200, at block 220, extracts the feature of interest 204 of the region of interest in the data portion 202. This may be achieved using a number of different methods. This will typically involve an intelligent parameterization of the data to produce parameters that vary when the event it is desired to detect occurs. For example, features such as peak height, peak width etc may be useful for some morphologies The system, at block 230 generates a probability density function ($PDF_n$) around the feature of interest 204 of the data portion $202_n$ expressing any uncertainties. This may be achieved using a number of different methods. For a recurrent feature of interest, this may be assessed by determining variability of the parameters across multiple samples of the feature of interest within the data portion $202_n$ The system, at block 240 combines $PDF_n$ and $PDF_{N-1}$ to create $PDF_N$ . . . . This may be achieved using a number of different methods.

The combination of PDFs can be considered as updating of knowledge. The $PDF_{N-1}$ can be considered as the prior knowledge. The $PDF_n$ can be considered as the likelihood. The $PDF_N$ can be considered as the posterior knowledge calculated using a Bayesian framework from $PDF_{N-1}$ and $PDF_n$. The prior knowledge $PDF_{N-1}$ is updated with the likelihood $PDF_n$ using the Bayesian framework to produce the posterior knowledge $PDF_N$. This may be the simple application of Bayes Theorem where a single parameter/PDF is assessed. In that case, $$PDF_N = k \cdot PDF_{N-1} * PDF_n.$$

where k is a normalization constant.

However, the Bayesian Framework may be more complex where multiple parameters are assessed. The Bayesian Framework may, for example, be represented as a directed acyclic graph.

The updated probability density $PDF_N$ may be based on a Bayesian framework for any form of probability density i.e. gamma, normal destruction etc. The exact form depends on the probability distribution used. The use of conjugate priors simplifies the form. Alternatively, combination may occur by means of Monte Carlo simulation or by taking the mean of parameters.

For a normal distribution, a PDF may be represented by a mean μ, and a variance $\sigma^2$.

$$\tilde{\mu} = \frac{\sigma_0^2}{\sigma_0^2 + \sigma^2/n} \overline{Y} + \frac{\sigma^2/n}{\sigma_0^2 + \sigma^2/n} \mu_0$$

$$\tilde{\sigma}^2 = \frac{\sigma_0^2 \sigma^2/n}{\sigma_0^2 + \sigma^2/n}$$

Where $\tilde{\mu}$ and $\tilde{\sigma}^2$ are the mean and variance of the posterior distribution after update, $\sigma_0^2$ is the old (previous) variance, $\sigma^2$ is the current variance, and n is the number of features in the current data, and $\overline{Y}$ is the current mean that is calculated using n number of features, and $\mu_0$ is the previous (old) mean.

For a normal distribution, a $PDF_i$ may be represented by a mean $\mu_i$, and a variance $\sigma^2_i$ Thus $$\mu_N = k1 * \mu_n + k2 * \mu_{N-1n}$$

where k1=a/(a+b), k2=b/(a+b)
$a = \sigma^2_o = \sigma^2_{N-1}$
$b = \sigma^2/n = \sigma^2 n/N_n$, where $N_n$ is the number of features used.
and $$\sigma^2 N = ab/(a+b)$$

The system 200, at block 232 generates an anomalous feature belief-network ($BN_{n=2}$) using probability density function ($PDF_{n=2}$) of the data portion $202_2$ and at block 242 generates an anomalous feature belief-network ($BN_{N=2}$) using probability density function $PDF_{N=2}$.

A belief network may, for example be generated from a window of the PDF e.g. a window centered on the mean and of total width X standard deviations, where X is a number, for example, greater than 1 and less than 4, for example 2.

One or more belief networks may be created for the existence of an anomaly (A) and also for the non-existence of an anomaly.

Although the classification blocks 250, 252 and the combine block 260 are illustrated as separate blocks they may in fact be part of a single process.

The blocks are designed to probabilistically combine simultaneously evidence that relates to different timescales e.g. local and global perspectives. There is a classification block 250, 252 . . . for each timescale (n−1, N−1) that classifies the same data portion $202_n$. The classification block, for each timescale, receives a different belief network $BN_{N-1}$, $BN_{n-1}$ that has been propagated from a previous iteration for data portion $202_{n-1}$.

For example marginalization may be used to combine probabilities relating to different belief networks.

Let us consider a Bayesian Framework for analyzing two competing hypotheses:
$H_1 = A =$ There is an anomaly
$H_2 = NA =$ there is no anomaly
A Bayesian Framework can be defined:

$$P(H_1 \mid D, I) = \frac{P(D \mid H_1, I)P(H_1 \mid I)}{[P(D \mid H_1, I)P(H_1 \mid I)] + [P(D \mid H_2, I)P(H_2 \mid I)]}$$

i.e.

$$P(A \mid D, I) = \frac{P(D \mid A, I)P(A \mid I)}{[P(D \mid A, I)P(A \mid I)] + [P(D \mid NA, I)P(NA \mid I)]}$$

Where knowledge expressed by the parameter K can be introduced in the likelihood as factorized as follows:
P(D, K|A, I)=P(D|K, A, I)P(K|A, I) and P(D, K|NA, I)=P (D|K, NA, I)P(K|NA, I)
P(A|D, I)=The probability of the hypothesis that there is an anomaly being true given the data, and all relevant background information necessary.
P(D|A, I)=The probability of the data D under the supposition that there is an anomaly A and any relevant background information I (likelihood).
P(D|NA, I)=The probability of the data D under the supposition that there is no anomaly NA and any relevant background information I (likelihood).

P(A|I)=The probability of the hypothesis that there is an anomaly (prior). This prior probability can be modified at any time based on evidence from an external source.
P(NA|I)=The prior probability of the hypothesis that there is no anomaly (prior). This prior probability can be modified at any time based on evidence from an external source.
P(D, K|A, I)=The joint probability of the data D and knowledge expressed by the introduced parameter K given the hypothesis that there is an anomaly A and any relevant background information I. The expression can be factorized as the product of P(D|K, A, I) and P(K|A, I). Marginalizing out the knowledge parameter K over discrete set of scenarios can be expressed as follows:

$$P(D,K \mid A,I) = \Sigma_{i=1}^{Q} P(D \mid K_i, A, I) P(K_i \mid A, I)$$

P(D, K|NA, I)=The joint probability of the data D and knowledge expressed by the introduced parameter K given the hypothesis that there is no anomaly NA and any relevant background information I. The expression can be factorized as the product of P(D|K, NA, I) and P(K|NA, I).

$$P(D,K \mid NA,I) = \Sigma_{i=1}^{Q} P(D \mid K_i, NA, I) P(K_i \mid NA, I)$$

D=The data is parametrized into one or more pieces of evidence referring to the relevant and distinct features in the signal In the example of FIG. 3, one timescale represented by $BN_n$ is local and relates to a short timescale e.g. the last data portion and another timescale represented by $BN_N$ is global and relates to a longer timescale e.g. all previous data portions or the previous 100 data portions, for example. $BN_n$ is the belief network determined for the data portion $202_n$ and $BN_N$ is the belief network determined for all the data portions up to and including data portion $202_n$. However, other belief networks can be used.

In this example the marginalized knowledge K relates to the different timescales. Thus Q represents the number of timescales. In this example 2, so:

The probability of an anomaly given the data (marginalized for the timescales) is:

$$P(A \mid D, I) = \frac{P(D \mid A, I)P(A \mid I)}{[P(D \mid A, I)P(A \mid I)] + [P(D \mid NA, I)P(NA \mid I)]}$$

where $$P(D, K \mid A, I) = [P(D \mid K_1, A)P(K_1 \mid A, I)] + [P(D \mid K_2, A)P(K_2 \mid A, I)]$$

$P(D|K_1, A)$ is the probability of the data portion $202_n$ given the belief network $BN_{N-1}$ for an anomaly where $P(K_1|A, I)$ is the prior probability for $BN_{N-1}$ which is independent from the data D and $P(D|K_2, A)$ is the probability of the data portion $202_n$ given the belief network $BN_{n-1}$ for an anomaly where $P(K_2|A, I)$ is the prior probability for $BN_{n-1}$ which is independent from the data D.

$$P(D,K \mid NA,I) = [P(D \mid K_1, NA)P(K_1 \mid NA, I)] + [P(D \mid K_2, NA)P(K_2 \mid NA, I)]$$

$P(D|K_1, NA)$ is the probability of the data portion $202_n$ given the belief network $BN_{N-1}$ for an anomaly where $P(K_1|NA, I)$ is the prior probability for $BN_{N-1}$ which is independent from the data D and $P(D|K_2, NA)$ is the probability of the data portion $202_n$ given the belief network $BN_{n-1}$ for an anomaly where $P(K_2|NA, I)$ is the prior probability for $BN_{n-1}$ which is independent from the data D.

In the above example, the marginalized knowledge K relates to the different timescales. Thus Q represents the number of timescales. However, marginalization may be used for other variables such as:
multiple different features of interest
multiple different parameters of a feature of interest
different methodologies for calculating likelihood
different methodologies for classification
different belief networks for each timescale The number of timescales may be a variable. It may, for example, be changed over time and be different for different data portions 202.

The number of timescales may be changed automatically based on the level of variability within the data. The number of timescales may be increased with increasing variability of data. Each timescale represents a different set of $N_m$ previous features of interest, for sets m=1 to M. Marginalisation may be used for the M sets.

M may be based on at least a variability of the current data portion $202_n$ compared to the previous data portion $202_{n-1}$. M may be determined based on a variability of probabilities that the event is present within the current feature of interest given a set $N_m$ of previous features of interest for each of the different sets m=1 to M.

In general form, the probability of an event (A) given the data (marginalized for the two timescales) is:

$$P(A \mid D, I) = \frac{P(D \mid A, I)P(A \mid I)}{[P(D \mid A, I)P(A \mid I)] + [P(D \mid NA, I)P(NA \mid I)]}$$

where $$P(D, K \mid A, I) = [P(D \mid K_1, A)P(K_1 \mid A, I)] + [P(D \mid K_2, A)P(K_2 \mid A, I)]$$

where $$P(K_1 \mid A, I) + P(K_2 \mid A, I) = 1$$

and $$P(A \mid D, I) + P(A \mid D, I) = 1$$

Thus, the probability that an event is present within a current feature of interest given the data containing the current features of interest and all relevant background information i.e. first (local) set of previous features of interest (P(A|D, I)) is based on: a probability of the current feature of interest given the event, based on the first (local) set of previous features of interest and its prior, [P(D|K$_1$, A, I)P(K$_1$|A, I)] and a probability of the event P(A|I). P(D|K$_1$, A) is a likelihood based on evidence (PDF$_{n-1}$, BN$_{n-1}$) from the first (local) set of previous features of interest and the current data portion $202_n$ (D). The likelihood is based on a likelihood of the current feature of interest given a belief BN$_{n-1}$ that is based on the first (local) set of previous features of interest (PDF$_{n-1}$). The previous PDF (PDF$_{n-1}$) is based on the first (local) set of previous features of interest and the belief BN$_{n-1}$ is based on the previous PDF (PDF$_{n-1}$).

Thus, the probability that an event is present within a current feature of interest given the data containing the current features of interest and all relevant background information i.e. second (global) set of previous features of interest (P(A|D, I)) is based on: a probability of the current feature of interest given the event, based on the second (global) set of previous features of interest and its prior, [P(D|K$_2$, A, I)P(K$_2$|A, I)] and a probability of the event P(A|I). P(D|K$_2$, A, I) is a likelihood based on evidence (PDF$_{N-1}$, BN$_{N-1}$) from the second (global) set of previous features of interest and the current data portion $202_n$ (D). The likelihood is based on a likelihood of the current feature of interest given a belief BN$_{N-1}$ that is based on the second (global) set of previous features of interest (PDF$_{N-1}$). The previous PDF (PDF$_{N-1}$) is based on the second (global) set of previous features of interest. For example, the previous PDF (PDF$_{N-1}$) may be based on a combination of PDFs and/or the previous PDF (PDF$_{N-1}$) may be based on a Bayesian update of a PDF (PDF$_{N-2}$). The belief BN$_{N-1}$ is based on the previous PDF (PDF$_{N-1}$).

Any of the parameters introduced in the likelihood (P(D|A, I)) for computing the probability that an event is present within a current feature of interest given the data D and any relevant background information (P(A|D, I)) may be marginalized with respect to multiple possible scenarios for the parameters. The multiple scenarios may, for example include, different belief networks for the timescales, different features of interest, different events, different classifications etc.

Thus, the probability that an event is present within a current feature of interest given a first set of previous features of interest is combined with the probability that the event is present within the current feature of interest given a second set of previous features of interest, different to the first set of previous features of interest.

The system 200, at block 270, detects the event based on the determined probability. The system 200, at block 280, conditionally controls performance of an action. If detection of the event has occurred at block 270, then the action is performed.

The event may, for example be an anomaly and the action may be an alert. The alert may be a visual, audio or electronic alert for example.

The data signals analysed for anomalies may be biological (bio) signals. The anomaly may be a marker for a health issue.

The data signals analysed for anomalies may be signals from measurements of mechanical machinery or other systems. The anomaly may be a marker for a fault, for example.

The iterative operation of the system 200 and method 100 will be now described with reference to FIG. 3. The iterative method enables Bayesian updating.

In each iteration n=m a belief network BN$_{n=m}$ and BD$_{N=M}$ is generated and propagated to the next iteration n=m+1, where they are used to classify the data portion $202_{m+1}$. Classification is a pre-cursor step to detecting an anomaly (block 270) and controlling performance of an action in dependence upon detection of an anomaly (block 280). Uncertainty in the feature of interest, represented by a combined probability density function PDF$_{N=M}$ is also generated at the iteration n=m and then propagated for use in the next iteration n=m+1, where it is used to detect a region of interest (block 210) and also used to generate the combined PDF for that iteration PDF$_{N=M+1}$.

Let us consider a flow of data to the system. The objective is to detect when anomalous data has been received by the system given a feature of interest, and control performance of an action.

At a first iteration, n=1:

At block 210, the method 100 comprises automatic detection of a relevant region of interest from data portion $202_1$.

At block 220, the method 100 comprises extract the feature of interest 204 of the region of interest 204 in the data portion $202_1$.

At block 230, the method 100 comprises generate a probability density function (PDF$_{n=1}$) around the feature of interest 204 of the data portion $202_1$ expressing any uncertainties.

At block 232, the method 100 comprises generate an anomalous feature belief-network ($BN_{n=1}$) using a probability density function ($PDF_1$) of the data portion $202_1$.

Then propagate $PDF_{n=1}$ and $BN_{n=1}$ to the next iteration.

At the next iteration, n=2:

At block 210, the method 100 comprises automatic detection of a relevant region of interest from data portion $202_2$ given $PDF_{n=1}$.

At block 252, the method 100 comprises probabilistically classify features of interest of the region of interest 204 in the data portion $202_2$ as anomalous/non-anomalous given the propagated belief network of the data portion $202_1$ ($BN_{n=1}$).

At block 220, the method 100 comprises extract the feature of interest 204 of the region of interest 204 in the data portion $202_2$.

At block 230, the method 100 comprises generate a probability density function ($PDF_{n=2}$) around the feature of interest 204 of the data portion $202_2$ expressing any uncertainties.

At block 240, the method 100 comprises combine $PDF_{n=1}$ and $PDF_{n=2}$ to create $PDF_{N=2}$.

At block 232, the method 100 comprises generate an anomalous feature belief-network ($BN_{n=2}$) using a probability density function ($PDF_{n=2}$) of the data portion $202_2$.

At block 242, the method 100 comprises generate an anomalous feature belief-network ($BN_{N=2}$) using probability density function $PDF_{N=2}$.

Then propagate $PDF_{N=2}$ and $BN_{N=2}$ $BN_{n=2}$ to the next iteration.

At the next iteration, n=3:

At block 210, the method 100 comprises automatic detection of a relevant region of interest from data portion $202_3$ given the propagated combined PDF, $PDF_{N=2}$.

At block 250, the method 100 comprises probabilistically classify features of interest of the region of interest 204 in the data portion $202_3$ as anomalous or non-anomalous given the propagated combined belief network of the previous data portions $202_1$, $202_2$ ($BN_{N=2}$).

At block 252 the method 100 comprises probabilistically classify features of interest of the region of interest 204 in the data portion $202_3$ as anomalous or non-anomalous given the propagated belief network of the immediately preceding data portion $202_2$ ($BN_{n=2}$).

At block 260, the method 100 comprises combine evidence from classification at block 250, 252.

Detection and conditional control occurs at blocks 270, 280.

At block 220, the method 100 comprises extract the feature of interest 204 of the region of interest 204 in the data portion $202_3$.

At block 230, the method 100 comprises generate a probability density function ($PDF_{n=3}$) around the feature of interest 204 of the data portion $202_3$ expressing any uncertainties.

At block 240, the method 100 comprises combine the propagated $PDF_{N=2}$ and generated $PDF_{n=2}$ to create $PDF_{N=3}$.

At block 232, the method 100 comprises generate an anomalous feature belief-network ($BN_{n=3}$) using probability density function ($PDF_{n=3}$) of the data portion $202_3$.

At block 242, the method 100 comprises generate an anomalous feature belief-network ($BN_{N=3}$) using the combined probability density function $PDF_{N=3}$.

Then propagate $PDF_{N=3}$ and $BN_{N=3}$ $BN_{n=3}$ to the next iteration.

At the next iteration, n=4:

At block 210, the method 100 comprises automatically detect a relevant region of interest from data portion $202_4$ given the propagated combined PDF, $PDF_{N=3}$.

At block 250, the method 100 comprises probabilistically classify features of interest of the region of interest 204 in the data portion $202_4$ as anomalous or non-anomalous given the propagated combined belief network of the previous data portions $202_1$, $202_2$, $202_3$ ($BN_{N=3}$).

At block 252, the method 100 comprises probabilistically classify features of interest of the region of interest 204 in the data portion $202_4$ as anomalous or non-anomalous given the propagated belief network of the immediately preceding data portion $202_3$ ($BN_{n=3}$).

At block 260, the method 100 comprises combine evidence from classification at block 250, 252.

Detection and conditional control occurs at blocks 270, 280.

At block 220, the method 100 comprises extract the feature of interest 204 of the region of interest 204 in the data portion $202_4$.

At block 230, the method 100 comprises generate probability density function ($PDF_{n=4}$) around the feature of interest 204 of the data portion $202_4$ expressing any uncertainties.

At block 240, the method 100 comprises combine the propagated $PDF_{N=3}$ and generated $PDF_{n=4}$ to create $PDF_{N=4}$.

At block 232, the method 100 comprises generate an anomalous feature belief-network ($BN_{n=4}$) using probability density function ($PDF_{n=4}$) of the data portion $202_4$.

At block 242, the method 100 comprises generate an anomalous feature belief-network ($BN_{N=4}$) using the combined probability density function $PDF_{N=4}$.

Then propagate $PDF_{N=4}$ and $BN_{N=4}$ $BN_{n=4}$ to the next iteration.

From the foregoing, it will be appreciated that in a current iteration (n), the system combines 240 a current PDF ($PDF_n$) based on the current feature of interest of the current data portion $202_n$ with a previous PDF ($PDF_{N-1}$) based on the set of previous features of interest to create, for the next iteration (n+1), a previous PDF ($PDF_N$) based on the set of previous features of interest. In the next iteration (n+1), the system uses the created previous PDF ($PDF_N$) in the creation of at least a probability ($PDF_{n+1}$) that an event is present within a current feature of interest of the data portion $202_{n+1}$ given a particular set of previous features of interest. The PDF ($PDF_n$) based on the current feature of interest is converted to a belief ($BN_n$) used in the next iteration Although the method 100 has been described with reference to probability density functions, it should be appreciated that instead of probability density functions any suitable measure of an expected relative likelihood of an occurrence of each value of a set of values for the particular parameter for parameterizing the signal may be used. Equivalents of PDFs should be interpreted accordingly.

The system 200, at block 220, extracts the feature of interest 204 of the region of interest in the data portion 202. This may be achieved using a number of different methods. In an example embodiment this comprises parameterization of the data to produce parameters that vary when the event it is desired to detect occurs. For example, features such as peak height, peak width etc may be useful for some morphologies In some but not necessarily all examples, the block 220 of the method 100, comprises parameterizing of the signal 202 based upon expected parameters that characterize a recurrent feature of interest of a biological signal. A distinction is made between the actual values (unknown) and expected or reference values. What actually characterizes an actual signal is different to what is expected to characterize an expected signal. Parameterization is based on expectation.

Figure 4A:
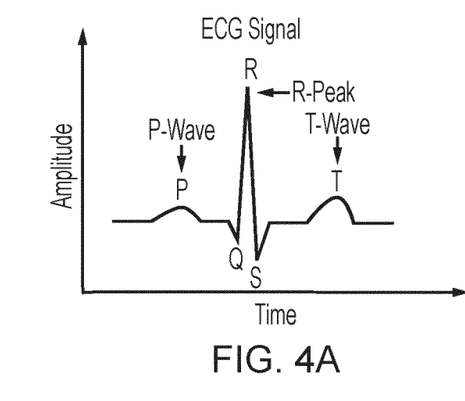
FIGS. 4A, 4B, 4C, 4D illustrate examples of a biological signal.
Figure 4B:
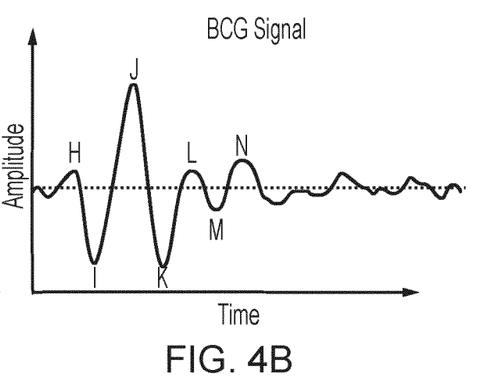
Figure 4C:
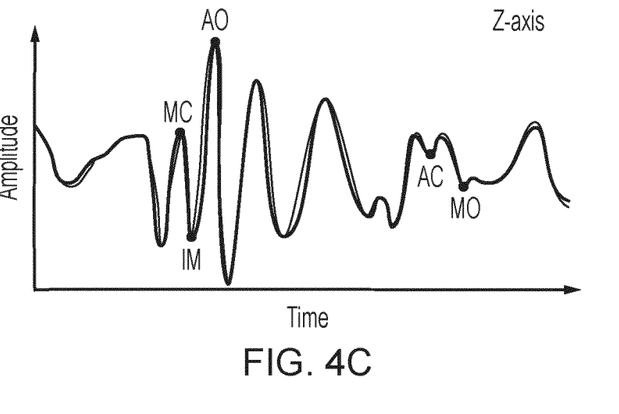
Figure 4D:
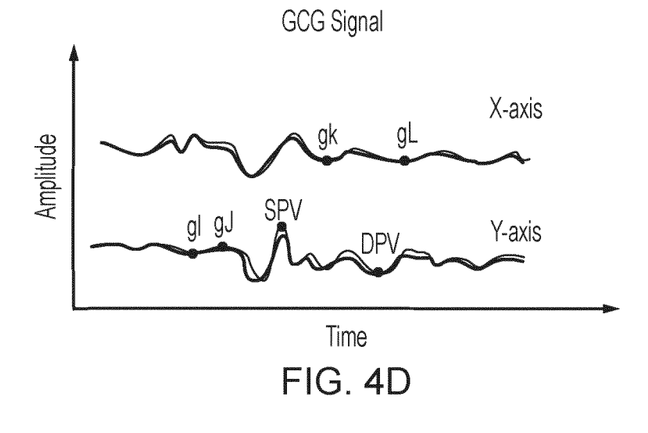

FIGS. 4A, 4B, 4C, 4D illustrate examples of a biological signal. A morphology of interest can be any recurrent morphology in a biological signal. FIG. 4A illustrates an example of an electrocardiogram (ECG) signal. FIG. 4B illustrates an example of a ballistocardiogram (BCG) signal. FIG. 4C illustrates an example of a seismocardiogram (SCG). FIG. 4D illustrates an example of a gyrocardiogram (GCG) signal. Gyrocardiography (GCG) is a non-invasive technique for assessing heart motions by utilizing a gyroscope that is attached to the chest of an individual as a sensor of angular motion.

Figure 5:
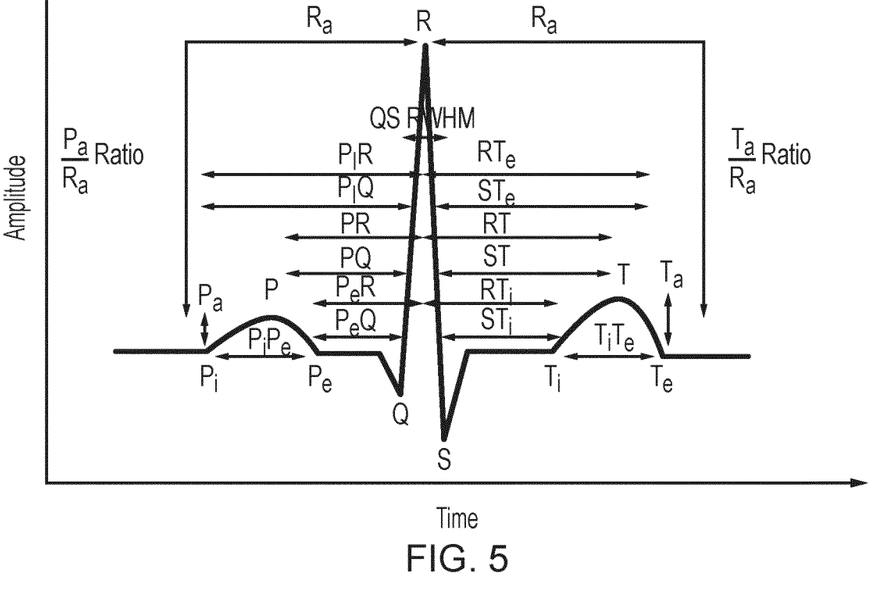
FIG. 5 illustrates an example of a parameterized electrocardiogram.

FIG. 5 illustrates an example of an electrocardiogram. The morphology of interest can be QRS-Complex and thus P-wave and T-wave are utilized as evidence. The morphology of interest can be T-wave and thus P-wave and QRS-complex are utilized as evidence. The morphology of interest can be P-wave and thus T-wave and QRS-complex are utilized as evidence The expected parameters may characterize a subject's heartbeat. The signal may be parameterized based upon expected parameters of an electrocardiogram signal.

The parameterization of the data portion 202 may be based upon parameters for an ECG signal. The parameters may be, as illustrated in FIG. 5:
Q=Starting point of QRS-Complex
R=Maximum point of QRS-Complex
S=End point QRS-Complex
$T_i$=Starting point of T-Wave
T=Maximum point of T-Wave
$T_e$=End point of T-Wave
$P_i$=Starting point of P-Wave
P=Maximum point of P-Wave
$R_a$=R peak amplitude
$P_a$=P wave amplitude
$T_a$=T wave amplitude
$P_e$=End point of P-Wave
$T_iT_e$=Distance between $T_i$ and $T_e$
$P_iP_e$=Distance between $P_i$ and $P_e$ $$\frac{T_a}{R_a} = \text{Ratio between } T \text{ amplitude and } R \text{ amplitude}$$

$$\frac{P_a}{R_a} = \text{Ratio between } P \text{ amplitude and } R \text{ amplitude}$$

PQ=Distance between P and Q
ST=Distance between S and T
$P_iT_e$=Distance between $P_i$ and $T_e$
RR=Distance between two consecutive R-Peaks Evidence may be determined based on the parameters
Evidence One ($E_1$)=QRS Morphology
Evidence Two ($E_2$)=$T_iTT_e$ Morphology
Evidence Three ($E_3$)=$P_iPP_e$ Morphology
Evidence Four ($E_4$)=$P_iT_e$ Morphology
Evidence Five ($E_5$)=$QT_e$ Morphology
Evidence Six ($E_6$)=$P_iS$ Morphology
Evidence Seven ($E_7$)=$R_a$
Evidence Eight ($E_8$)=$P_a$
Evidence Nine ($E_9$)=$T_a$ $$\text{Evidence Ten}(E_{10}) = \frac{T_a}{R_a} \text{ Ratio}$$

$$\text{Evidence Eleven}(E_{11}) = \frac{P_a}{R_a} \text{ Ratio}$$

Evidence Twelve ($E_{12}$)=QS FWHM
Evidence Thirteen ($E_{13}$)=$P_iR$
Evidence Fourteen ($E_{14}$)=$T_iQ$
Evidence Fifteen ($E_{15}$)=PR
Evidence Sixteen ($E_{16}$)=PQ
Evidence Seventeen (E17)=$P_eR$
Evidence Eighteen ($E_{18}$)=$P_eQ$
Evidence Nineteen ($E_{19}$)=$RT_e$
Evidence Twenty ($E_{20}$)=$ST_e$
Evidence Twenty One ($E_{21}$)=RT
Evidence Twenty Two ($E_{22}$)=ST
Evidence Twenty Three ($E_{23}$)=$RT_i$
Evidence Twenty Four ($E_{24}$)=$ST_i$
Evidence Twenty Five ($E_{25}$)=$T_e$
Evidence Twenty Six ($E_{26}$)=$P_e$
Evidence Twenty Seven ($E_{27}$)=RR
Evidence Twenty Eight ($E_{28}$)=$P_iT_e$ All evidence, including $E_1$ up to $E_{28}$ can be utilized. Alternatively or additionally, any combinations of evidence can be utilized. E.g. $E_1$-$E_5$, $E_2$-$E_{20}$, $E_{20}$-$E_{28}$ etc.

Alternatively or additionally, any number of newly generated features that utilize any combinations of evidence can be utilized. E.g. $E_1$ combined with $E_2$-$E_1$, $E_2$, $E_1$, $E_2$ and $E_3$ combined—$E_1E_2E_3$ etc.

Figure 6:
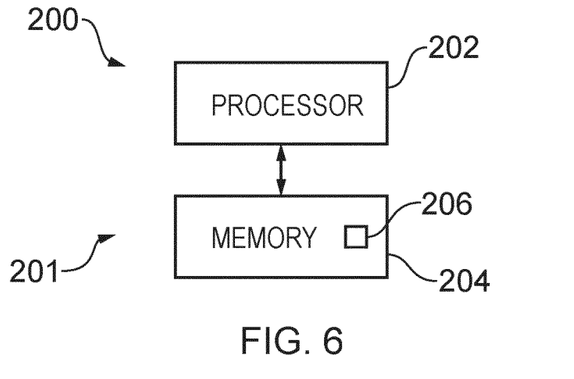
FIG. 6 illustrates an example of an apparatus comprising means for performing the method.

FIG. 6 illustrates an example of an apparatus 200 comprising means for performing the method 100 as described above.

The apparatus 200 may, for example, comprise a controller 201. The apparatus 200 is, in some but not necessarily all examples, a monitoring apparatus that measures features of a signal, to assess the health or fitness of a system. The monitoring apparatus 200 may as a consequence of the performance of the method 100 detect anomalies in a signal. The signal may be received from one or more sensors comprised in the apparatus 200.

The apparatus 200 is, in some but not necessarily all examples, a health monitoring apparatus that measures features of a biological signal, to assess the health or fitness of a subject. The health monitoring apparatus 200 may as a consequence of the performance of the method 100 detect anomalies in a biological signal. The biological signal may be received from one or more sensors comprised in the apparatus 200

Implementation of a controller 201 may be as controller circuitry. The controller 201 may be implemented in hardware alone, have certain aspects in software including firmware alone or can be a combination of hardware and software (including firmware).

As illustrated in FIG. 6 the controller 201 may be implemented using instructions that enable hardware functionality, for example, by using executable instructions of a computer program 206 in a general-purpose or special-purpose processor 202 that may be stored on a computer readable storage medium (disk, memory etc) to be executed by such a processor 202.

The processor 202 is configured to read from and write to the memory 204. The processor 202 may also comprise an output interface via which data and/or commands are output by the processor 202 and an input interface via which data and/or commands are input to the processor 202.

The memory 204 stores a computer program 206 comprising computer program instructions (computer program code) that controls the operation of the apparatus 200 when loaded into the processor 202. The computer program instructions, of the computer program 206, provide the logic and routines that enables the apparatus to perform the methods illustrated in FIG. 1. The processor 202 by reading the memory 204 is able to load and execute the computer program 206.

The apparatus 200 therefore comprises:
at least one processor 202; and
at least one memory 204 including computer program code
the at least one memory 204 and the computer program code configured to, with the at least one processor 202, cause the apparatus 200 at least to perform:
producing a determined probability by combining:
  a probability that an event is present within a current feature of interest given a first set of previous features of interest, wherein the current feature of interest is a feature of interest of a current data portion and
  a probability that the event is present within the current feature of interest given a second set of previous features of interest, different to the first set of previous features of interest and wherein the previous features of interest are the feature of interest of previous data portions;
detecting the event based on the determined probability; and
in dependence on detecting the event, controllably performing an action.

The computer program 206 may arrive at the apparatus 200 via any suitable delivery mechanism. The delivery mechanism may be, for example, a non-transitory computer-readable storage medium, a computer program product, a memory device, a record medium such as a Compact Disc Read-Only Memory (CD-ROM) or Digital Versatile Disc (DVD), an article of manufacture that tangibly embodies the computer program 206. The delivery mechanism may be a signal configured to reliably transfer the computer program 206. The apparatus 200 may propagate or transmit the computer program 206 as a computer data signal.

The computer program 206 when run on a processor enables the processor to control performance of an action in dependence upon detection of an event by performing or causing:
determining a probability by combining:
  a probability that an event is present within a current feature of interest given a first set of previous features of interest, wherein the current feature of interest is a feature of interest of a current data portion and
  a probability that the event is present within the current feature of interest given a second set of previous features of interest, different to the first set of previous features of interest and wherein the previous features of interest are the feature of interest of previous data portions;
detecting the event based on the determined probability; and
in dependence on the detection of the event, controllably performing an action.

Although the memory 204 is illustrated as a single component/circuitry it may be implemented as one or more separate components/circuitry some or all of which may be integrated/removable and/or may provide permanent/semi-permanent/dynamic/cached storage.

Although the processor 202 is illustrated as a single component/circuitry it may be implemented as one or more separate components/circuitry some or all of which may be integrated/removable. The processor 202 may be a single core or multi-core processor.

The methods and apparatus described above may be used to detect automatically an anomaly in recurrent features of interest within a signal, for example, a biological signal.

Such automation reduces or eliminates the need for a trained human expert to review the signal and converts the signal as measured to an intelligently parameterized signal is a form that is machine readable and machine processable. The signal is intelligently parameterized based on the recurrent features of interest that define that signals morphology.

The signal, parameterized based on its recurrent features of interest, may be used as an input to further processes.

These processes may occur locally or remotely. They may, for example, be cloud based.

The processes may enable health monitoring applications when it may be desirable to measure features of a biological signal, to assess the health or fitness of a subject.

Alternatively, or additionally, the processes may enable a warning to be generated that alerts a subject or someone else. The warning may, for example, warn the subject or someone else that an anomaly has been detected or that a threshold has been exceeded. The warning may be an audible warning. The warning may be a message communicated through a communication system.

The apparatus may, for example, be a personal, wearable apparatus.

The apparatus may, for example, be a health monitor apparatus or a vital-signs monitor apparatus.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as Field-Programmable Gate Arrays (FPGA), Application Specific Integrated Circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:
(a) hardware-only circuit implementations (such as implementations in only analog and/or digital circuitry) and
(b) to combinations of circuits and software (and/or firmware), such as (as applicable):
(i) to a combination of processor(s) or (ii) to portions of processor(s)/software (including digital signal processor(s)), software, and memory(ies) that work together to cause an apparatus, such as a mobile phone or server, to perform various functions and
(c) to circuits, such as a microprocessor(s) or a portion of a microprocessor(s), that require software or firmware for operation, even if the software or firmware is not physically present.

This definition of 'circuitry' applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

The blocks illustrated in FIG. 1 may represent steps in a method and/or sections of code in the computer program 206. The illustration of a particular order to the blocks does not necessarily imply that there is a required or preferred order for the blocks and the order and arrangement of the block may be varied. Furthermore, it may be possible for some blocks to be omitted.

As used here 'module' refers to a unit or apparatus that excludes certain parts/components that would be added by an end manufacturer or a user. the apparatus 10 may be a module.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one" or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
   at least one processor; and
   at least one non-transitory memory storing instructions, that when executed by the at least one processor, cause the apparatus to at least:
   determine with a biological signal for monitoring a health or fitness of a subject a probability by combining time-separated sequences for each of a plurality of data portions measured at a period of time exclusive to each data portion comprising at least:
   a probability that an event associated with the biological signal is present within a current feature of interest at a first time-separated sequence of the time-separated sequences given a first set of previous features of interest, and
   a probability that the event is present within the current feature of interest given a second set of previous features of interest at a second time-separated sequence that is different to the first set of previous features of interest and is not overlapping the first time-separated sequence;
   detect the event based on the determined probability, wherein the detected event is an anomaly for the health or fitness of the subject; and
   to control, in dependence on the detection of the event, an action comprising providing an alert that the anomaly has been detected.

2. An apparatus as claimed in claim 1, wherein the first set of previous features of interest is smaller than the second set of previous features of interest.

3. An apparatus as claimed in claim 1, wherein the first set of previous features of interest consists of an immediately previous feature of interest and the second set of previous features of interest consists of a sequence of immediately previous features of interest.

4. An apparatus as claimed in claim 1, wherein the probability that an event is present within a current feature of interest given a first set of previous features of interest, is
   based on a probability of the current feature of interest given the event,
   based on the first set of previous features of interest, and
   based on a probability of the event.

5. An apparatus as claimed in claim 1, wherein the probability that an event is present within a current feature of interest given a first set of previous features of interest is based on:
   a likelihood based on evidence from the first set of previous features of interest and a current data portion, and a probability of the event.

6. An apparatus as claimed in claim 1, wherein the probability that the event is present within the current feature of interest given a second set of previous features of interest, different to the first set of previous features of interest is
   based on a probability of the current feature of interest given the event,
   based on the second set of previous features of interest, and
   based on a probability of the event.

7. An apparatus as claimed in claim 1, wherein the probability that the event is present within the current feature of interest given a second set of previous features of interest, different to the first set of previous features of interest is based on:
   a likelihood based on evidence from the second set of previous features of interest and the current data portion, and a probability of the event.

8. An apparatus as claimed in any claim 7, wherein the likelihood is based on a previous probability density function wherein the previous probability density function is based on the second set of previous features of interest.

9. An apparatus as claimed in claim 8, wherein the previous probability density function is based on a combination of probability density functions and/or the previous probability density function is based on a Bayesian update of a probability density function.

10. An apparatus as claimed in claim 1, wherein the probability that an event is present within a current feature of interest given a first set of previous features of interest is marginalized with respect to multiple scenarios for the event and wherein the probability that the event is present within the current feature of interest given a second set of previous features of interest is marginalized with respect to the same multiple scenarios for the event.

11. An apparatus as claimed in claim 1, wherein combining the probability that an event is present within a current feature of interest given a first set of previous features of interest and the probability that the event is present within the current feature of interest given a second set of previous features of interest, different to the first set of previous features of interest, is part of combining a probability that an event is present within a current feature of interest given a different set of $N_m$ previous features of interest, for a number of different sets m=1 to M, wherein the combined probabilities are marginalized with respect to the different sets.

12. An apparatus as claimed in claim 11, wherein the at least one non-transitory memory including the computer program code is configured with the at least one processor to cause the apparatus to vary the number of different sets M.

13. An apparatus as claimed in claim 1, wherein the at least one non-transitory memory including the computer program code is configured with the at least one processor to cause the apparatus to:
  in a current iteration, combine a current probability density function based on the current feature of interest with a previous probability density function based on a set of previous features of interest to update, for a next iteration, the previous probability density function based on the set of previous features of interest and
  in the next iteration, use the updated previous probability density function in the creation of at least a probability that an event is present within a current feature of interest given a particular set of previous features of interest.

14. An apparatus as claimed in claim 1, wherein the alert is a visual, audio or electronic alert that comprises an indication that a threshold for the health or fitness of the subject has been exceeded.

15. An apparatus as claimed in claim 1, comprising a system monitoring apparatus, wherein the detected event is indicative of an anomaly in the system or failure of the system and wherein the system monitoring apparatus is configured to generate as an output an alert signal indicative of an anomaly in or failure of the system.

16. An apparatus as claimed in claim 1, comprising an electrocardiogram sensor, wherein the detected event is indicative of an anomaly in a sensed electrocardiogram by the electrocardiogram sensor.

17. A method, comprising:
  controlling performance of an action in dependence upon detection of an event comprising: determining with a biological signal for monitoring a health or fitness of a subject a probability by combining time-separated sequences for each of a plurality of data portions measured at a period of time exclusive to each data portion comprising:
    a probability that an event associated with the biological signal is present within a current feature of interest at a first time-separated sequence of the time-separated sequences given a first set of previous features of interest, wherein the current feature of interest is a feature of interest of a current data portion, and
    a probability that the event is present within the current feature of interest given a second set of previous features of interest at a second time-separated sequence that is different to the first set of previous features of interest and is not overlapping the first time-separated sequence and wherein the previous features of interest are the feature of interest of previous data portions;
  detecting the event based on the determined probability, wherein the detected event is an anomaly for the health or fitness of the subject; and
  in dependence on the detection of the event, controllably performing an action comprising providing an alert that the anomaly has been detected.

18. An apparatus, comprising:
  at least one processor; and
  at least one non-transitory memory storing instructions, that when executed by the at least one processor, cause the apparatus at least to:
  in dependence upon detection of an event performing or causing:
    determining with a biological signal for monitoring a health or fitness of a subject a probability by combining time-separated sequences for each of a plurality of data portions measured at a period of time exclusive to each data portion comprising:
      a probability that an event is present within a current feature of interest given a first set of previous features of interest, wherein the current feature of interest is a feature of interest of a current data portion, and
      a probability that the event is present within the current feature of interest given a second set of previous features of interest at a second time-separated sequence that is different to the first set of previous features of interest and is not overlapping the first time-separated sequence, and wherein the previous features of interest are the feature of interest of previous data portions;
    detecting the event based on the determined probability, wherein the detected event is an anomaly for the health or fitness of the subject; and
  in dependence on the detection of the event, controllably performing an action comprising providing an alert that the anomaly has been detected.

\* \* \* \* \*